United States Patent
Schroers et al.

(10) Patent No.: US 9,645,218 B2
(45) Date of Patent: May 9, 2017

(54) METHOD AND DEVICE FOR TESTING SENSORS TO BE APPLIED ON A PATIENT'S SKIN FOR THE DETECTION OF FLUID OR MOISTURE

(71) Applicant: Fresenius Medical Care Deutschland GmbH, Bad Homburg v.d.H (DE)

(72) Inventors: Alexander Schroers, Frankfurt (DE); John Heppe, St. Wendel (DE); Roland Rullof, Lebach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 518 days.

(21) Appl. No.: 14/012,326

(22) Filed: Aug. 28, 2013

(65) Prior Publication Data
US 2014/0059837 A1    Mar. 6, 2014

Related U.S. Application Data

(60) Provisional application No. 61/695,358, filed on Aug. 31, 2012.

(30) Foreign Application Priority Data

Aug. 31, 2012   (DE) .......... 10 2012 017 205

(51) Int. Cl.
    *G01R 35/00*   (2006.01)
    *A61B 5/02*    (2006.01)
    (Continued)

(52) U.S. Cl.
    CPC .......... *G01R 35/00* (2013.01); *A61B 5/02042* (2013.01); *A61B 5/1495* (2013.01);
    (Continued)

(58) Field of Classification Search
    CPC ................... A61B 5/00; G01R 35/00
    (Continued)

(56) References Cited

U.S. PATENT DOCUMENTS

| | | | | |
|---|---|---|---|---|
| 4,638,346 A | * | 1/1987 | Inami | G01N 27/286 257/253 |
| 5,036,859 A | * | 8/1991 | Brown | A61F 5/48 128/886 |

(Continued)

FOREIGN PATENT DOCUMENTS

| | | |
|---|---|---|
| DE | 10 2007 006274 A1 | 8/2008 |
| DE | 10 2010 012545 A1 | 9/2011 |

(Continued)

OTHER PUBLICATIONS

International Preliminary Report on Patentability dated Mar. 3, 2015 in PCT/EP2013/002486.

(Continued)

*Primary Examiner* — Peter DungBa Vo
*Assistant Examiner* — Kaying Kue
(74) *Attorney, Agent, or Firm* — Kilyk & Bowersox, P.L.L.C.

(57) ABSTRACT

A method and device for testing sensors to be applied on a patient's skin for detection of liquid or moisture are described, in particular for monitoring vascular access in an extracorporeal blood treatment, in which a patient's blood is carried away from the patient via an arterial line and is fed to the patient via a venous line. A method for producing sensors to be applied on a patient's skin for detection of liquid or moisture is also described. The method and device according to the present invention are based on the testing of one or more moisture sensors which are taken from current production. The method includes providing a large number of twists of the moisture sensor applied onto a torsion body, (Continued)

the mechanical stresses thus recreating the stresses that can occur in practice when the moisture sensor is applied or stuck onto the patient's skin or forearm.

13 Claims, 3 Drawing Sheets

(51) Int. Cl.
| | |
|---|---|
| A61M 1/36 | (2006.01) |
| G01R 3/00 | (2006.01) |
| A61B 5/1495 | (2006.01) |
| A61F 13/42 | (2006.01) |
| G01M 3/16 | (2006.01) |
| A61B 5/00 | (2006.01) |
| A61F 13/00 | (2006.01) |

(52) U.S. Cl.
CPC .............. *A61B 5/443* (2013.01); *A61F 13/42* (2013.01); *A61M 1/3653* (2013.01); *A61M 1/3656* (2014.02); *G01M 3/16* (2013.01); *G01R 3/00* (2013.01); *A61B 5/6831* (2013.01); *A61B 2562/029* (2013.01); *A61B 2562/12* (2013.01); *A61F 2013/00429* (2013.01); *A61M 2209/02* (2013.01); *Y10T 29/49004* (2015.01)

(58) Field of Classification Search
USPC .............................. 29/593, 705; 73/73, 29.01
See application file for complete search history.

(56) References Cited

U.S. PATENT DOCUMENTS

| | | | |
|---|---|---|---|
| 5,948,994 | A | 9/1999 | Jen et al. |
| 6,461,329 | B1* | 10/2002 | Van Antwerp .... A61M 5/16836 604/111 |
| 7,605,710 | B2* | 10/2009 | Crnkovich .............. A61F 13/42 340/603 |
| 2002/0198483 | A1 | 12/2002 | Wariar et al. |
| 2005/0275547 | A1* | 12/2005 | Kates ..................... G08B 19/00 340/605 |
| 2008/0041792 | A1* | 2/2008 | Crnkovich .............. A61F 13/42 210/739 |
| 2009/0182244 | A1* | 7/2009 | Hoenes ............ G01N 33/48778 600/583 |
| 2012/0130330 | A1* | 5/2012 | Wilson ................... A61F 13/42 604/361 |
| 2012/0234078 | A1* | 9/2012 | Hagl ...................... A61B 5/441 73/29.02 |

FOREIGN PATENT DOCUMENTS

| | | |
|---|---|---|
| WO | 2006 008866 A1 | 1/2006 |
| WO | 2010/091852 A1 | 8/2010 |
| WO | 2011/116943 A1 | 9/2011 |

OTHER PUBLICATIONS

International Search Report dated Oct. 23, 2013 in PCT/EP2013/002486.
www.muehlbauer.sk_1, "Epassport Qualification Systems".
www.muehlbauer.sk_2, "Card Quality Control Tools".

\* cited by examiner

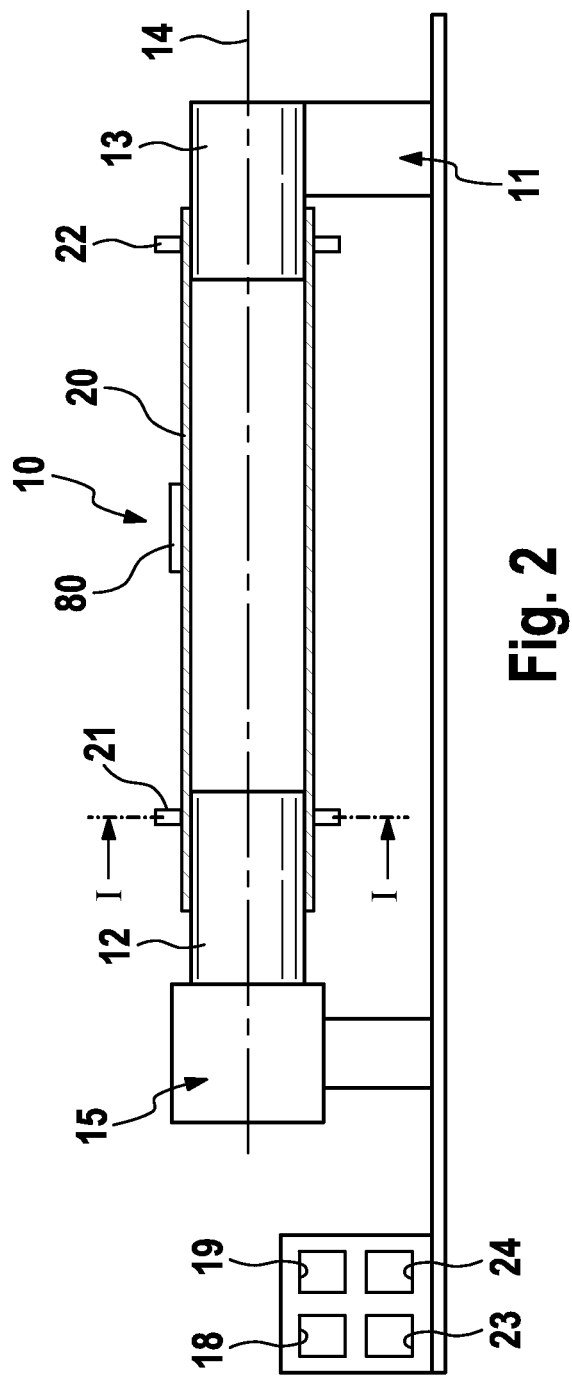
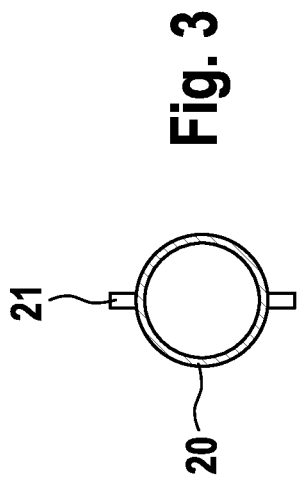

METHOD AND DEVICE FOR TESTING SENSORS TO BE APPLIED ON A PATIENT'S SKIN FOR THE DETECTION OF FLUID OR MOISTURE

CROSS REFERENCE TO RELATED APPLICATIONS

The present application claims priority to U.S. Provisional Application Ser. No. 61/695,358, filed on Aug. 31, 2012, and claims priority to Application No. DE 10 2012 017 205.2, filed in the Federal Republic of Germany on Aug. 31, 2012, the entire contents of which are incorporated herein in their entirety by reference thereto.

FIELD OF INVENTION

The present invention relates to a method and a device for testing sensors to be applied on a patient's skin for the detection of liquid or moisture, in particular moisture sensors for monitoring the vascular access in an extracorporeal blood treatment, wherein a patient's blood is carried away from the patient via an arterial hose line comprising an arterial cannula and is fed to the patient via a venous hose line comprising a venous puncture cannula. Moreover, the present invention relates to a method for producing sensors to be applied on a patient's skin for the detection of liquid or moisture.

BACKGROUND INFORMATION

International Patent Publication No. WO 2011/116943 describes a moisture sensor for monitoring a vascular access, which is constituted as a textile planar structure of non-conductive warp threads and non-conductive weft threads as well as conductive warp threads and conductive weft threads. The non-conductive warp and weft threads and the conductive warp and weft threads are disposed in the fabric such that an electrically conductive structure with electrical terminals results. The electrical resistance between the terminals is measured in order to detect fluid on moisture. If the fabric is wetted with fluid, the electrical resistance changes so that the fluid is detected.

International Patent Publication No. WO 2010/091852 describes a textile moisture sensor for monitoring a vascular access, wherein the electrically conductive structure with the electrical terminals is printed onto the fabric.

Apart from resistive sensors, capacitive moisture sensors are also known, which comprise an electrically conductive structure made up of a plurality of electrically conductive sections.

The known moisture sensors for monitoring a vascular access, which comprise an electrically conductive structure made up of a plurality of conductive sections, permit monitoring of the functioning capability by the fact that the electrical properties of the sensor are measured under defined conditions and compared with properties preset as a reference value. If the divergences between the measured properties and the properties preset as a reference value exceed or fall below a preset amount, for example, due to a rupture of a strip conductor or a short circuit, it is concluded that there is a faulty moisture sensor.

The known textile moisture sensors are applied on the patient's skin at the puncture point. To monitor a vascular access in an extracorporeal blood treatment, the moisture sensors are stuck, for example, on the patient's forearm. The forearm with a vascular access is generally kept still by the patient during the extracorporeal blood treatment. If, however, the patient moves the forearm during the blood treatment, the moisture sensor is subjected to mechanical stresses, so that the conductive sections of the electrically conductive structure are repeatedly subjected to tensile, compressive or bending stresses. The problem of the mechanical stress arises in the case of textile moisture sensors, wherein warp and weft threads form the electrically conductive structure. There is, however, a risk of rupture of a strip conductor due to micro-cracks also in the case of printed strip conductors.

Textile moisture sensors with woven or printed strip conductors have the advantage that the sensors can be produced cost-effectively in large numbers on a common fabric web. The individual moisture sensors are separated from one another after the weaving and, if necessary, further processing steps.

SUMMARY

A problem underlying the present invention is to provide a method for the production of moisture sensors with an electrically conductive structure comprising a plurality of electrically conductive sections in large quantities, wherein the produced moisture sensors meet high quality requirements.

A further problem underlying the present invention consists in providing a method for the quality control of moisture sensors with an electrically conductive structure comprising a plurality of electrically conductive sections.

Furthermore, a problem underlying the present invention is to provide a device which permits a reliable quality control of the moisture sensors.

The method according to the present invention and the device according to the present invention are based on the destructive testing of one or more moisture sensors, which are removed from current production as a sample. The present invention provides for complex mechanical stressing of the moisture sensors which is modelled on stresses occurring in practice when the moisture sensor is applied, in particular stuck, onto the patient's skin, in particular on a forearm. The mechanical stresses that occur in the most unfavourable case can be simulated. In the case where the moisture sensor or sensors of a batch do not comply with the set requirements in the test, it is concluded that the batch is faulty. Further samples can then be taken or the whole batch can be rejected.

It has been shown in tests that the mechanical stresses on the moisture sensor on the patient's skin can be simulated if the moisture sensor is applied to a deformable body which is repeatedly deformed. Alternating tensile, compressive and bending stresses thereby arise in the moisture sensor, which can lead to corresponding reversible and irreversible deformations in the microscopic range and even to rupture of the strip conductors. The test thus corresponds to artificial stressing under realistic conditions, wherein a preset number of alternating load cycles is generated. The moisture sensor can be stuck onto the surface of the elastic body. Any other kind of fixing of the moisture sensor is, however, also possible. The important thing is that the moisture sensor is firmly connected with its underside to the upper side of the elastic body.

Furthermore, it has been shown in tests that a particularly realistic simulation of the mechanical stresses occurring during the wearing of the moisture sensor is possible when the moisture sensor is applied onto the surface of an elastic torsion body and the torsion body is repeatedly twisted, for example twisted in an oscillating manner. A cylindrical torsion body, on the lateral surface whereof the moisture sensor is applied, is particularly preferred.

During the extracorporeal blood treatment, in particular haemodialysis treatment, the patient generally holds his arm such that the palm faces upwards. It has been realised that maximum stressing of the moisture sensor can occur in practice only when the patient turns his arm through 180°, so that the palm faces downwards. With the twisting of the cylindrical torsion body through an angle of 180°, it is thus possible to recreate the maximum freedom of movement of the arm in a realistic manner.

The test according to the present invention provides for twisting of a torsion body through a preset torsion angle, which preferably lies between 60° to 180°, in particular between 80° to 160°, preferably between 100° to 140°. Moreover, the test according to the present invention provides for a number of twists, which lies between 100 and 1000, in particular between 200 to 800, preferably between 400 to 600 twists. The effect of this is that the moisture sensor is subjected to relatively large alternating load cycles which can lead to destruction of the sensor.

The torsion body is preferably clamped fixedly at one end, and is twisted at the other end through a preset angle of rotation. It is, however, also possible to twist the torsion body at both ends in opposite angles of rotation.

The method according to the present invention and the device according to the present invention offer particular advantages particularly in the testing of moisture sensors which are constituted as a textile planar structure comprising non-conductive warp threads and non-conductive weft threads as well as conductive warp threads and conductive weft threads, wherein the non-conductive warp and weft threads and conductive warp and weft threads are disposed such that the electrically conductive structure is formed. The method according to the present invention and the device according to the present invention can, however, also be used for the quality control of moisture sensors comprising a carrier material, onto which the electrically conductive structure is applied, preferably printed. In principle, the method according to the present invention and the device according to the present invention are suitable for testing all kinds of plaster sensors and also plasters dispensing medication.

For the present invention, it is in principle unimportant which electrical properties are compared with a reference value for the quality control. For example, the electrical resistance is measured in the case of resistive moisture sensors and the capacitance in the case of capacitive moisture sensors. The electrical properties can be measured before and/or after the alternating stress cycle and/or during the mechanical alternating stress cycle. The characteristic properties can also be measured before the alternating stress cycle in order to establish the reference value. For example, it is possible for the measurement values ascertained before and after the alternating stress cycle to be compared with one another and subjected to a statistical evaluation.

It has been shown in tests that moisture sensors applied, in particular stuck, onto the surface of the elastic body cannot be removed again or can be removed only with difficulty. The device according to the present invention for performing the method according to the present invention therefore provides an operating unit for the interchangeable accommodation of the elastic body, said operating unit being constituted such that the elastic body is deformed. After the testing of the moisture sensor, the elastic body can simply be discarded with the moisture sensor and a new elastic body, onto which the moisture sensor is applied, can be inserted again into the operating unit.

The device according to the present invention comprises a measuring unit for measuring the electrical properties of the moisture sensors and an evaluation unit for evaluating the measurement results of the measuring unit.

A particularly preferred exemplary embodiment provides a hose as a torsion body. This elastic body approximates most closely to a patient's arm. In particular, stretching and compressing of the patient's skin can be simulated particularly realistically by the hose. The mechanical stresses can be varied in a selective manner through the material thickness and/or the material properties of the hose. In another exemplary embodiment, it is in principle also possible to use a hose which has only relatively small material thickness. The mechanical properties required for testing the moisture sensor can in this case be produced by the fact that the hose is inflated with compressed air. A compressed air unit can be provided for this purpose, which supplies compressed air via a compressed air supply line to the hose closed airtight at both ends. The compressed air unit can be provided on the rotatable and/or fixed body, to which the hose ends can be attached in an airtight manner, wherein the compressed air can be supplied via a channel in the rotatable and/or fixed body.

In the preferred exemplary embodiment, which provides a hose as a torsion body, the operating unit preferably comprises a rotatable cylindrical body to which one end of the hose can be attached and a fixed cylindrical body to which the other end of the hose can be attached. It is, however, also possible for the two cylindrical bodies of the operating unit to be twisted against one another.

In a further particularly preferred exemplary embodiment, the control unit is constituted such that the operating unit performs a preset number of twists of the torsion body. The control unit is preferably constituted such that the operating unit performs the twists through a preset torsion angle. The number of twists and the torsion angle can be inputted on an input unit or can be provided permanently in the control unit. The control unit can provide for automatic control of the overall test sequence.

Exemplary embodiments of the present invention are explained in greater detail below with reference to the accompanying drawings.

BRIEF DESCRIPTION OF THE DRAWINGS

FIG. 2 shows a simplified diagrammatic representation of an exemplary embodiment of the device for performing a test on moisture sensors.

FIG. 3 shows a cross-section through the device along line I-I of FIG. 2.

DETAILED DESCRIPTION

Figure 1:
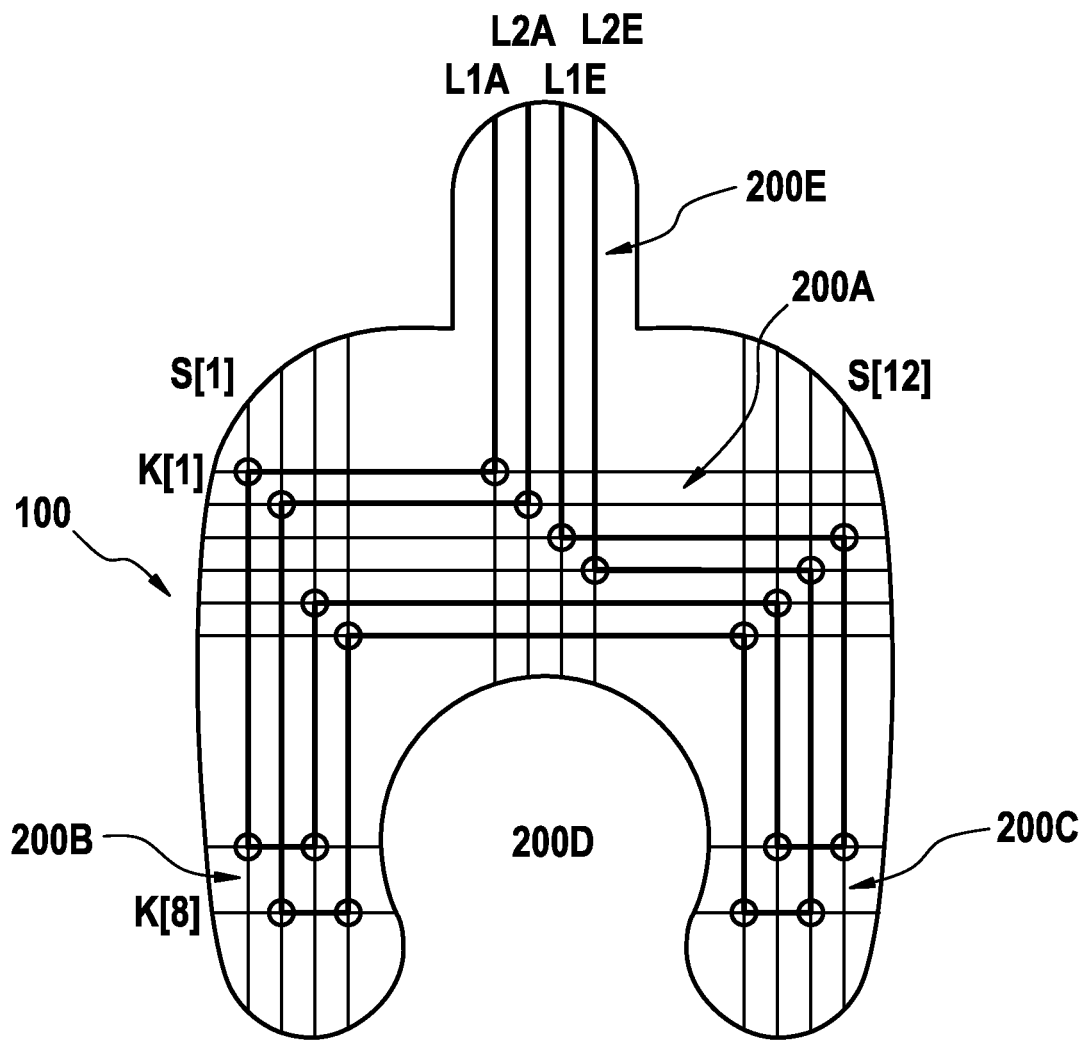
FIG. 1 shows an exemplary embodiment of a textile moisture sensor in a simplified diagrammatic representation.

FIG. 1 shows in plan view an exemplary embodiment of a woven moisture sensor 100 for monitoring a vascular access. The moisture sensor, which can be treated as a plaster, is stuck onto the patient's skin. The moisture sensor is stuck onto the patient's forearm to monitor an arterial or venous vascular access in extracorporeal blood treatment.

Moisture sensor 100 is constituted as a pad of a textile planar structure to be placed onto the patient's skin. The textile planar structure is a fabric comprising electrically conductive and electrically non-conductive warp and weft threads. The electrically conductive warp and weft threads are disposed at the points of intersection such that an electrically conductive structure is formed.

The moisture sensor comprises a central zone 200A with two legs 200B, 200C, which laterally enclose a semicircular cutout 200D. A tab 200E lying opposite the two legs is formed on the central zone. The electrically conductive warp and weft threads forming a structure of electrical strip conductors are characterised by horizontal and vertical thin lines. Weft threads S run in the vertical direction and warp threads K run in the horizontal direction. The strip conductor structure is formed by eight warp threads K [1] to K [8] and twelve weft threads S [1] to S [12], which are disposed at the points of intersection such that they are either connected in an electrically conductive manner or are insulated electrically from one another.

In FIG. 1, the electrical contact points at the points of intersection between the electrically conductive warp and weft threads K[i], S [i] are represented as circles. First strip conductor L1A-L1E runs from tab 200E via central zone 200A to left-hand leg 200B and from the left-hand leg via the central zone to right-hand leg 200C and from the right-hand leg via the central zone back to the tab of the pad. The start of the respective strip conductor is designated by "A" and the end of the strip conductor is designated by "E". The two ends L1A, L1E of first strip conductor L1A-L1E form a first pair of terminals. Second strip conductor L2A-L2E runs from tab 200E via central zone 200A to left-hand leg 200B and from the left-hand leg via the central zone to right-hand leg 200C and from the right-hand leg via the central zone to the tab of pad. The two ends L2A, L2E of second strip conductor L2A-L2E form a second pair of terminals. The electrical resistance is measured between terminals L1A and L2E, whilst terminals L1E and L2A are connected to an electrical terminal resistor not represented.

The moisture sensor described by reference to FIG. 1 is described in detail in International Patent Publication No. WO 2011/116943, the contents of which are incorporated herein in its entirety by reference thereto.

FIG. 2 shows, in a simplified diagrammatic representation, an exemplary embodiment of a device 10 for testing moisture sensors, which can in particular be textile moisture sensors with woven or printed strip conductors. A particularly preferred use is in the testing of woven moisture sensors of the type described by reference to FIG. 1, which are stuck onto the patient's forearm.

Device 10 comprises a frame 11, on which two cylindrical bodies 12, 13, for example mandrels, are disposed spaced apart from one another on a common axis 14. One of the two cylindrical bodies 13 is fixed immobile on frame 11, whilst the other cylindrical body 12 is disposed on the frame so as to be rotatable about axis 14. In FIG. 2, left-hand cylindrical body 12 is mounted so as to be rotatable about axis 14 and right-hand cylindrical body 13 is connected fixedly to frame 11.

Device 10 comprises an operating unit 15 (represented only diagrammatically) for rotatable cylindrical body 12. Operating unit 15 preferably driven by electric motor or pneumatically permits a rotation of cylindrical body 12 in the clockwise and counterclockwise directions through a preset angle of rotation.

Operating unit 15 is controlled by a control unit 18. Control unit 18 controls operating unit 15 such that the operating unit performs a preset number of rotations of cylindrical body 12 within a test cycle, wherein the rotation in the clockwise direction through a preset angle is followed each time by a rotation in the counterclockwise direction through a preset angle.

The number of rotations and the size of the angle of rotation can be inputted on input unit 19. The maximum angle of rotation is limited to 120° in the exemplary embodiment. For a test cycle, cylindrical body 12 can be rotated counterclockwise out of its initial position, for example through 120°, within a preset time interval, for example 2 seconds, and then clockwise, for example through 120°, back into the initial position, wherein the rotation in the clockwise and counterclockwise directions is repeated by control unit 18 within the test cycle after the lapse of a preset time interval, until such time as a preset number of rotations, for example 500 cycles, or alternating load cycles, have been performed.

The two cylindrical bodies 12, 13 serve to fix a hose 20, the internal diameter whereof corresponds to the external diameter of the cylindrical bodies, so that the hose can be pushed in a matching manner onto the cylindrical bodies. The hose is fixed at both ends by means of fixing means 21, 22 represented only in outline in FIG. 2, so that the ends of the hose surround the cylindrical bodies in an airtight manner. In the simplest case, fixing means 21, 22 can be cable binders. For example, FIG. 3 shows a cross-section through the device along line I-I of FIG. 2. For automatic operation of the device, however, automatically operating fixing means, for example driven pneumatically or by electric motor, are provided, which can be controlled by the control unit.

When the ends of the hose are fixed on cylindrical bodies 12, 13, the rotary motion of the left-hand cylindrical body leads to twisting of hose 20 through the preset torsion angle.

A patient's forearm during the dialysis treatment can be replicated by repeatedly twisting hose 20. An average treatment time of 8 hours is assumed in the present exemplary embodiment. The hose diameter should correspond to the average diameter of the forearm.

In order to ascertain an optimum deflection angle, a grid was drawn on a test subject's forearm, the forearm being placed with the palm facing upwards, which corresponds to an angle of rotation of 0°. The grid was then measured as the forearm was rotated through 180°, the palm facing downwards. A deformation of the lines running at right angles to one another appeared. This deformation of the grid lines was replicated by twisting the hose on which the same grid was drawn with the same dimensions, the hose being twisted by means of the device through a specific torsion angle. An optimum agreement of the grid lines on the patient's forearm and the hose appeared with a torsion angle of 120°.

Moreover, the device comprises a measuring unit 23 for measuring the electrical properties of moisture sensor 80, which was applied centrally on the hose 20. The measurement results were evaluated in an evaluation unit 24 of the device according to known methods.

Figure 4:
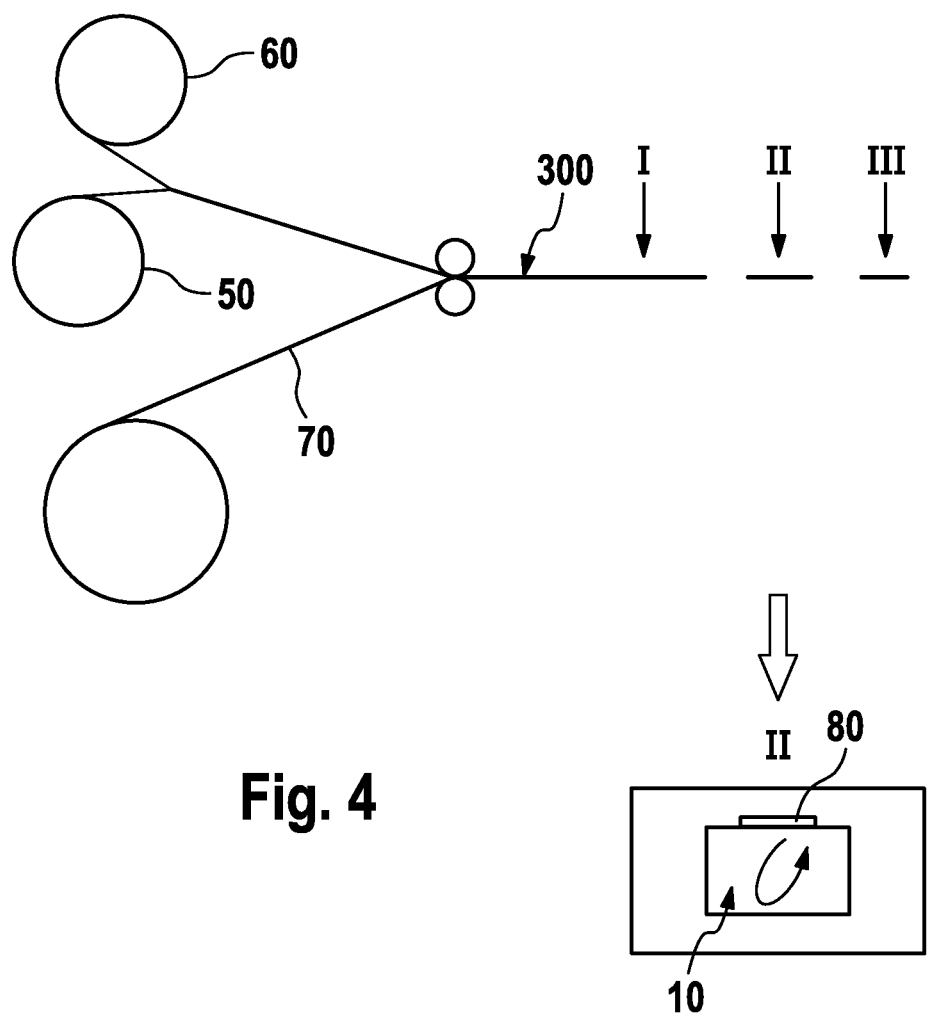
FIG. 4 shows a very simplified diagrammatic representation of the process steps for producing the moisture sensor.

FIG. 4 shows the main process steps for producing moisture sensors to be tested, in a very simplified diagrammatic representation according to the production method according to the present invention. Warp threads 50 and weft threads 60 are fed to produce a fabric web 300 with a large number of moisture sensors, which each comprise a woven electrically conductive structure. After the production of the fabric comprising conductive and non-conductive warp and weft threads, further process steps known to the person skilled in the art take place. They include, for example, the finishing, in particular the washing, fixing and heat treatment. During the weaving process, a layer 70 is fed, with which fabric web 300 is lined. Layer 70 is applied on the underside of fabric web 300. The individual moisture sensors are then separated in a further process step I. The moisture sensors are tested in a further process step II. The sensors are finally made up in process step III.

The method described above for producing woven moisture sensors belongs to the prior art, with the exception of the inventive testing of the moisture sensors. This production method is described in detail in International Patent Publication No. WO 2011/116943, the contents of which are incorporated herein in its entirety by reference thereto.

The testing of the moisture sensors with the test method according to the present invention is described below. The test method according to the present invention provides for a final control (EK) during ongoing production in process step II. One or more sensors 80 are removed from a batch of produced moisture sensors for a random sample in order to test the sensors with device 10 according to the present invention. Moisture sensor 80 to be tested is stuck centrally onto the lateral surface of hose 20. The hose is then inserted into operating unit 15, wherein the ends of the hose are pushed onto cylindrical bodies 12, 13 fixed by means of fixing means 21, 22. The test cycle is then started, wherein the hose and the moisture sensor are subjected to a preset number of twists, preferably 400 to 600 twists, through a preset torsion angle, preferably approx. 120°.

The electrical properties of moisture sensor 80 are measured with measuring unit 23 and evaluated with evaluation unit 24, wherein the measured properties are compared with properties preset as a reference value. In the case of a deviation by a preset amount, it is deduced that the moisture sensor is faulty. Evaluation unit 24 preferably comprises a display unit, on which the result of the test is displayed or logged. In the present exemplary embodiment for testing the woven moisture sensors, the measured property is the electrical resistance between the terminals concerned or a magnitude correlating with the resistance. Consequently, the electrical resistance is measured. The measured resistance values can be evaluated statistically. For example, the resistance values can be compared with an upper and a lower threshold value, it being concluded that there is a faulty moisture sensor if the measured resistance lies outside the threshold value range.

The device according to the present invention permits the acquisition of measurement values before, during and/or after one or more twists; with measurements before the twists, corresponding comparative values can also be ascertained for a preferably statistical evaluation.

What is claimed is:

1. A method for testing sensors to be applied on a patient's skin for detection of liquid or moisture, the sensors comprising an electrically conductive structure with electrical terminals, wherein electrical properties of the sensors are measured under defined conditions and compared with electrical properties preset as a reference value, the method comprising:
    removing at least one sensor from production,
    applying the at least one sensor onto a surface of an elastic body, wherein the elastic body is an elastic torsion body,
    repeatedly deforming the elastic body, wherein the repeatedly deforming includes repeatedly twisting, and
    after the repeated deformation of the elastic body, comparing the measured electrical properties with the preset electrical properties,
    determining that the at least one sensor is faulty based on deviations between the measured electrical properties and the preset electrical properties of the at least one sensor.

2. The method according to claim 1, wherein the torsion body is clamped fixedly at one end and is twisted through a preset angle of rotation at another end.

3. The method according to claim 1, wherein the torsion body is a cylindrical body, on a lateral surface whereof the at least one sensor is applied.

4. The method according to claim 1, wherein the torsion body is a hose.

5. The method according to claim 1, wherein a plurality of sensors is removed from a batch of the production, and the deviations between the measured electrical properties and the preset electrical properties of the plurality of sensors removed from the batch are evaluated statistically.

6. The method according to claim 1, wherein the torsion body is twisted through a torsion angle of between 60° to 180°, between 80° to 160°, or between 100° to 140°.

7. The method according to claim 1, wherein a number of twists is between 100 and 1000 twists.

8. The method according to claim 1, wherein a number of twists is between 200 to 800 twists.

9. The method according to claim 1, wherein a number of twists is between 400 to 600 twists.

10. A method for producing and testing sensors to be applied on a patient's skin for detection of moisture, the sensors comprising an electrically conductive structure with electrical terminals, the method comprising:
    producing a plurality of sensors disposed beside one another on a common web,
    separating the plurality of sensors into single units, and
    performing testing on at least one sensor of the plurality, according to a testing method that comprises:
        applying the at least one sensor onto a surface of an elastic body, wherein the elastic body is an elastic torsion body,
        repeatedly deforming the elastic body, wherein the repeatedly deforming includes repeatedly twisting,
        after the repeated deformation of the elastic body, comparing the measured electrical properties with the preset electrical properties, and
        determining that the at least one sensor is faulty based on deviations between the measured electrical properties and the preset electrical properties of the at least one sensor.

11. The method according to claim 10, wherein the sensors are resistive moisture sensors that measure electrical resistance or a magnitude correlating with the electrical resistance.

12. The method according to claim 10, wherein the sensors are configured as a textile planar structure comprising non-conductive warp threads and non-conductive weft threads and conductive warp threads and conductive weft threads, wherein the non-conductive warp threads and weft threads and the conductive warp threads and weft threads are disposed such that the electrically conductive structure is formed.

13. The method according to claim 10, wherein the sensors comprise a carrier material, onto which the electrically conductive structure is applied or printed.

* * * * *